US009234868B2

(12) United States Patent
Ishiguro et al.

(10) Patent No.: US 9,234,868 B2
(45) Date of Patent: Jan. 12, 2016

(54) NO$_x$ SENSOR CONTROL APPARATUS AND VEHICLE CONTROL APPARATUS

(75) Inventors: Yasuhiro Ishiguro, Komaki (JP); Takayuki Sumi, Nagoya (JP); Akihiro Kobayashi, Nisshin (JP); Hisashi Sasaki, Konan (JP); Koji Shiotani, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 1153 days.

(21) Appl. No.: 12/398,008

(22) Filed: Mar. 4, 2009

(65) Prior Publication Data
US 2009/0223820 A1 Sep. 10, 2009

(30) Foreign Application Priority Data

Mar. 5, 2008 (JP) ................................. 2008-54432

(51) Int. Cl.
G01N 27/406 (2006.01)
G01N 27/419 (2006.01)

(52) U.S. Cl.
CPC .......... *G01N 27/4065* (2013.01); *G01N 27/419* (2013.01)

(58) Field of Classification Search
CPC ..................................... G01N 27/406–27/419
USPC ...................... 204/424–429; 205/783.5–785; 73/23.31–23.32
See application file for complete search history.

(56) References Cited

U.S. PATENT DOCUMENTS 5,249,453 A * 10/1993 Usami et al. ............... 73/23.32
6,214,207 B1 4/2001 Miyata et al.
6,352,632 B1 * 3/2002 Inagaki et al. ............. 204/425
2002/0017467 A1 * 2/2002 Ando et al. ................. 205/781
2002/0162743 A1 * 11/2002 Inagaki ....................... 204/425
2008/0237064 A1 * 10/2008 Nakasone et al. .......... 205/781

FOREIGN PATENT DOCUMENTS

| JP | 10-142194 A | 5/1998 |
| JP | 2846735 B2 | 10/1998 |
| JP | 11-304758 A | 11/1999 |
| WO | WO 2007119311 A1 * | 10/2007 |

* cited by examiner

*Primary Examiner* — J. Christopher Ball
*Assistant Examiner* — Maris R Kessel
(74) *Attorney, Agent, or Firm* — Sughrue Mion, PLLC

(57) ABSTRACT

An NO$_X$ sensor control apparatus (10) is connected to an NO$_X$ sensor (100) which includes a first pumping cell (110) and a second pumping cell (130) through which a second pumping current flows corresponding to an NO$_X$ concentration in a to-be-measured gas. The NO$_X$ sensor control apparatus (10) includes a first pumping current detection unit; a second pumping current detection unit; an oxygen concentration calculation unit (60) for calculating oxygen concentration on the basis of the first pumping current and corrected in accordance with the pressure of the to-be-measured gas, oxygen (first) pressure correction information set for the NO$_X$ sensor, and pressure information; and an NO$_X$ concentration calculation unit (60) for calculating NO$_X$ concentration on the basis of the first pumping current and corrected in accordance with pressure of the to-be-measured gas, NO$_X$ (second) pressure correction information set for the NO$_X$ sensor, and pressure information.

3 Claims, 6 Drawing Sheets

FIG. 3

| RANK | NOX PRESSURE CORRECTION COEFFICIENT (k1) |
|---|---|
| 0 | 10 |
| 1 | 14 |
| 2 | 18 |
| 3 | 22 |
| 4 | 26 |
| 5 | 30 |
| 6 | 34 |
| 7 | 38 |

NO$_X$ SENSOR CONTROL APPARATUS AND VEHICLE CONTROL APPARATUS

BACKGROUND OF THE INVENTION

1. Field of the Invention

The present invention relates to an NO$_X$ sensor control apparatus (e.g., controller) which is connected to an NO$_X$ sensor and which controls the NO$_X$ sensor, and to a vehicle control apparatus (e.g., ECU) connected to the NO$_X$ sensor control apparatus.

2. Description of the Related Art

A known gas sensor for measuring the concentration of a specific gas component in the exhaust gas of an automobile includes at least one cell composed of a solid electrolyte member and a pair of electrodes provided thereon. The gas sensor is configured such that one electrode of the cell faces a measurement chamber into which the exhaust gas flows. In such a gas sensor, the gas concentration is measured based on an output from the electrode pair of the cell, and the measurement is stabilized by limiting (controlling) the amount of the gas which flows into the measurement chamber under a predetermined diffusion resistance. However, this conventional gas sensor poses a problem in that the amount of gas which flows into the measurement chamber changes in accordance with a change in pressure of the exhaust gas in the vicinity of the attached gas sensor. Further, the output changes even when the concentration of the specific gas remains unchanged, such that the measured gas concentration is subject to measurement error.

In view of the above, a technique has been developed for an air-fuel-ratio sensor which includes an internal space into which the gas to be measured is introduced under a predetermined diffusion resistance, and first and second electrochemical cells each composed of a solid electrolyte member and a pair of electrodes. According to this technique, when a sensor output y0 indicating oxygen concentration is corrected on the basis of the detected pressure Pg of the gas to be measured, a gas pressure variation index B, previously measured for an individual air-fuel-ratio sensor, is taken into consideration (see, for example, Patent Document 1).

In recent years, NO$_X$ sensors have been developed for detecting the NO$_X$ concentration of a to-be-measured gas by use of a solid electrolyte member. Further, an NO$_X$ sensor has been developed which can measure both NO$_X$ concentration and oxygen concentration (i.e., which can function as the above-described air-fuel-ratio sensor) and a control apparatus for controlling this type of sensor (see, for example, Patent Documents 2 and 3). In this NO$_X$ sensor, a to-be-measured gas is introduced into a first measurement chamber under a predetermined diffusion resistance, and the oxygen concentration of the to-be-measured gas is adjusted to a predetermined concentration by means of a first pumping cell composed of a solid electrolyte member and a pair of first electrodes. The to-be-measured gas having the adjusted oxygen concentration flows from the first measurement chamber into an NO$_X$ measurement chamber. Further, NO$_X$ contained in the to-be-measured gas is decomposed by means of a second pumping cell composed of a solid electrolyte member and a pair of second electrodes, whereby a second pumping current corresponding to the NO$_X$ concentration flows between the pair of second electrodes. In this manner, in the technique described in Patent Documents 2 and 3, the NO$_X$ concentration is calculated based on the second pumping current flowing through the second pumping cell, and the oxygen concentration is calculated based on the first pumping current flowing through the first pumping cell. Notably, in the technique disclosed in Patent Document 3, in order to correct the oxygen-concentration dependency of the second pumping current, the NO$_X$ concentration is finally determined in consideration of the first pumping current (oxygen concentration) and the second pumping current.

[Patent Document 1] Japanese Patent No. 2846735 (claim 2)

[Patent Document 2] Japanese Patent Application Laid-Open (kokai) No. 10-142194 (abstract, claim 1)

[Patent Document 3] Japanese Patent Application Laid-Open (kokai) No. 11-304758

3. Problems to Be Solved by the Invention

However, a technique has not yet been developed for correcting both NO$_X$ concentration information and oxygen concentration information obtained by use of an NO$_X$ senor, in accordance with the pressure of a to-be-measured gas. Further, the pressure dependency of the sensor output (first pumping current and second pumping current) varies among individual NO$_X$ sensors. Therefore, if a pressure-dependent variation in the sensor output or a concentration value calculated on the basis of the sensor output is corrected uniformly, the degree of correction varies among the individual NO$_X$ sensors. Finally, the NO$_X$ concentration information and the oxygen concentration information may vary among the individual NO$_X$ sensors. Notably, the reason why the pressure dependency of the sensor output or the concentration value varies among the individual NO$_X$ sensors is that the magnitude of the diffusion resistance, which acts on oxygen introduced into the first measurement chamber, varies due to changes in production conditions (hereinafter referred to as production variations).

Further, since the second pumping current used for calculating the NO$_X$ concentration has an oxygen concentration dependency, in the technique disclosed in Patent Document 3, the second pumping current is corrected based on the oxygen concentration (oxygen concentration calculated on the basis of the first pumping current). However, the gas pressure dependency of the oxygen concentration itself, which is used for making the correction, is not taken into consideration.

SUMMARY OF THE INVENTION

Accordingly, an object of the present invention is to provide an NO$_X$ sensor control apparatus and a vehicle control apparatus which correct both NO$_X$ concentration information and oxygen concentration information in accordance with the pressure of a to-be-measured gas so as to reflect the pressure dependency of sensor output, which pressure dependency varies among individual NO$_X$ sensors, to thereby enable accurate measurement of NO$_X$ concentration and oxygen concentration using a single NO$_X$ sensor, irrespective of a change in the pressure of the to-be-measured gas.

In order to solve the above-described problems, the present invention provides an NO$_X$ sensor control apparatus connectable to an NO$_X$ sensor, the NO$_X$ sensor comprising a first pumping cell which has paired first electrodes provided internally and externally, respectively, of a first measurement chamber and which pumps oxygen out of a to-be-measured gas introduced into the first measurement chamber or pumps oxygen into the first measurement chamber to thereby adjust oxygen concentration in the first measurement chamber; and a second pumping cell which has paired second electrodes provided internally and externally, respectively, of an NO$_X$ measurement chamber in communication with the first measurement chamber, the second pumping cell being configured such that a second pumping current flows between the paired second electrodes, the second pumping current corresponding to $NO_X$ concentration of the to-be-measured gas having flowed from the first measurement chamber into the $NO_X$ measurement chamber and having an adjusted oxygen concentration. The $NO_X$ sensor control apparatus includes a first pumping current detector for detecting a first pumping current flowing between the paired first electrodes of the first pumping cell; a second pumping current detector for detecting a second pumping current flowing between the paired second electrodes of the second pumping cell; an oxygen concentration calculation unit for calculating oxygen concentration of the to-be-measured gas based on the first pumping current and corrected in accordance with pressure of the to-be-measured gas, first pressure correction information (information used for correcting the oxygen concentration based on the pressure of the to-be-measured gas) set for the $NO_X$ sensor (preferably for each individual $NO_X$ sensor), and externally input pressure information representing the pressure of the to-be-measured gas; and an $NO_X$ concentration calculation unit for calculating $NO_X$ concentration of the to-be-measured gas based on the second pumping current and corrected in accordance with the pressure of the to-be-measured gas, second pressure correction information (information used for correcting the $NO_X$ concentration on the basis of the pressure of the to-be-measured gas) set for the $NO_X$ sensor (preferably for each individual $NO_X$ sensor), and the pressure information.

By virtue of this configuration, the $NO_X$ concentration information and the oxygen concentration information can be corrected in accordance with the pressure of the to-be-measured gas. Further, in the case where the respective pressure dependencies of the $NO_X$ concentration information and the oxygen concentration information are previously measured for each individual $NO_X$ sensor and the measured pressure dependency is stored as an oxygen pressure correction coefficient (the first pressure correction information) and an $NO_X$ pressure correction coefficient (the second pressure correction information), the pressure dependencies of the $NO_X$ concentration information and the oxygen concentration information which vary among the individual sensors can be reflected in the correction. In this manner, the $NO_X$ concentration and the oxygen concentration can be accurately determined by use of a single $NO_X$ sensor irrespective of the pressure of the to-be-measured gas.

Notably, the term "$NO_X$ concentration information" as used herein corresponds to the second pumping current which flows in accordance with the $NO_X$ concentration, and an $NO_X$ concentration value calculated from the second pumping current. Accordingly, in the present invention, in order to correct the $NO_X$ concentration information in accordance with the pressure of the to-be-measured gas, the second pumping current may be corrected in accordance with the pressure, or the $NO_X$ concentration value may be corrected in accordance with the pressure. Further, the term "oxygen concentration information" as used herein corresponds to the first pumping current and an oxygen concentration value calculated from the first pumping current. Accordingly, in the present invention, in order to correct the oxygen concentration information in accordance with the pressure of the to-be-measured gas, the first pumping current may be corrected in accordance with the pressure, or the oxygen concentration value may be corrected in accordance with the pressure.

Preferably, the $NO_X$ concentration calculation unit calculates the $NO_X$ concentration of the to-be-measured gas corrected in accordance with the pressure of the to-be-measured gas, based on the second pumping current, the second pressure correction information, the pressure information, and the corrected oxygen concentration calculated by the oxygen concentration calculation unit.

By virtue of this configuration, when the $NO_X$ concentration value is calculated using the oxygen concentration as well as the second pumping current in order to correct for the oxygen concentration dependency of the second pumping current, the pressure compensated oxygen concentration is used. Therefore, the influence of pressure change on oxygen concentration is eliminated, and a more accurate correction for eliminating the oxygen concentration dependency can be performed. As a result, an accurate $NO_X$ concentration value is obtained.

The first pressure correction information and the second pressure correction information may be stored in a storage unit associated with the $NO_X$ sensor.

When this configuration is employed, the processing for storing an oxygen pressure correction coefficient (the first pressure correction information) and an $NO_X$ pressure correction coefficient (the second pressure correction information) in the $NO_X$ sensor control apparatus becomes unnecessary. The oxygen pressure correction coefficient and the $NO_X$ pressure correction coefficient are stored in the storage unit provided on the $NO_X$ sensor side when the $NO_X$ sensor undergoes a shipment inspection or a production inspection. Therefore, these coefficients are not required to be measured in a different work step, and thus the work load can be reduced. Notably, the storage unit provided may be provided at any location on the $NO_X$ sensor side as long as the storage is not damaged by heat. Preferably, the storage unit is provided within or in the vicinity of a connector of the $NO_X$ sensor used for connecting the $NO_X$ sensor to the $NO_X$ sensor control apparatus.

As used herein, "$NO_X$ sensor side" means within or in the vicinity of the $NO_X$ sensor, and physically located closer to the $NO_X$ sensor and farther from the $NO_X$ sensor control apparatus. As mentioned above, the storage unit associated with the $NO_X$ sensor may be provided in a connector (signal/power connector) for connecting the $NO_X$ sensor to the $NO_X$ sensor control apparatus.

A vehicle control apparatus of the present invention communicates with an $NO_X$ sensor control apparatus connectable to an $NO_X$ sensor, the $NO_X$ sensor comprising a first pumping cell which has paired first electrodes provided internally and externally, respectively, of a first measurement chamber and which pumps oxygen out of a to-be-measured gas introduced into the first measurement chamber or pumps oxygen into the first measurement chamber to thereby adjust oxygen concentration in the first measurement chamber; and a second pumping cell which has paired second electrodes provided internally and externally, respectively, of an $NO_X$ measurement chamber, the second pumping cell being configured such that a second pumping current flows between the paired second electrodes, the second current corresponding to $NO_X$ concentration of the to-be-measured gas having flowed from the first measurement chamber into the $NO_X$ measurement chamber and having an adjusted oxygen concentration. The $NO_X$ sensor control apparatus includes a first pumping current detector for detecting a first pumping current flowing between the paired first electrodes of the first pumping cell; and a second pumping current detector for detecting a second pumping current flowing between the paired second electrodes of the second pumping cell. The vehicle control apparatus comprises a receiving unit for receiving from the $NO_X$ sensor control apparatus the first pumping current, the second pumping current, first pressure correction information (information used for correcting the oxygen concentration based on the pressure of to-be-measured gas) set for the $NO_X$ sensor and second pressure correction information (information used for correcting the $NO_X$ concentration based on the pressure of to-be-measured gas) set for the $NO_X$ sensor; an oxygen concentration calculation unit for calculating oxygen concentration of the to-be-measured gas based on the first pumping current and corrected in accordance with pressure of the to-be-measured gas, the first pressure correction information, and externally input pressure information representing the pressure of the to-be-measured gas; and an $NO_X$ concentration calculation unit for calculating $NO_X$ concentration of the to-be-measured gas based on the second pumping current and corrected in accordance with pressure of the to-be-measured gas, the second pressure correction information, and the pressure information.

Preferably, the $NO_X$ concentration calculation unit calculates the $NO_X$ concentration of the to-be-measured gas corrected in accordance with the pressure of the to-be-measured gas, based on the second pumping current, the second pressure correction information, the pressure information, and the corrected oxygen concentration calculated by the oxygen concentration calculation unit.

Effect of the Invention

According to the present invention, both the $NO_X$ concentration information and the oxygen concentration information are corrected in accordance with the pressure of the to-be-measured gas, and variation in pressure dependency of the $NO_X$ concentration information and the oxygen concentration information among individual $NO_X$ sensors is also factored into the correction, whereby the $NO_X$ concentration and the oxygen concentration can be accurately obtained using a single $NO_X$ sensor, irrespective of the pressure of the to-be-measured gas.

BRIEF DESCRIPTION OF THE DRAWINGS

FIG. 3 is a table representing a map showing $NO_X$ pressure correction coefficient ($k_1$).

DESCRIPTION OF REFERENCE NUMERALS

Figure 1:
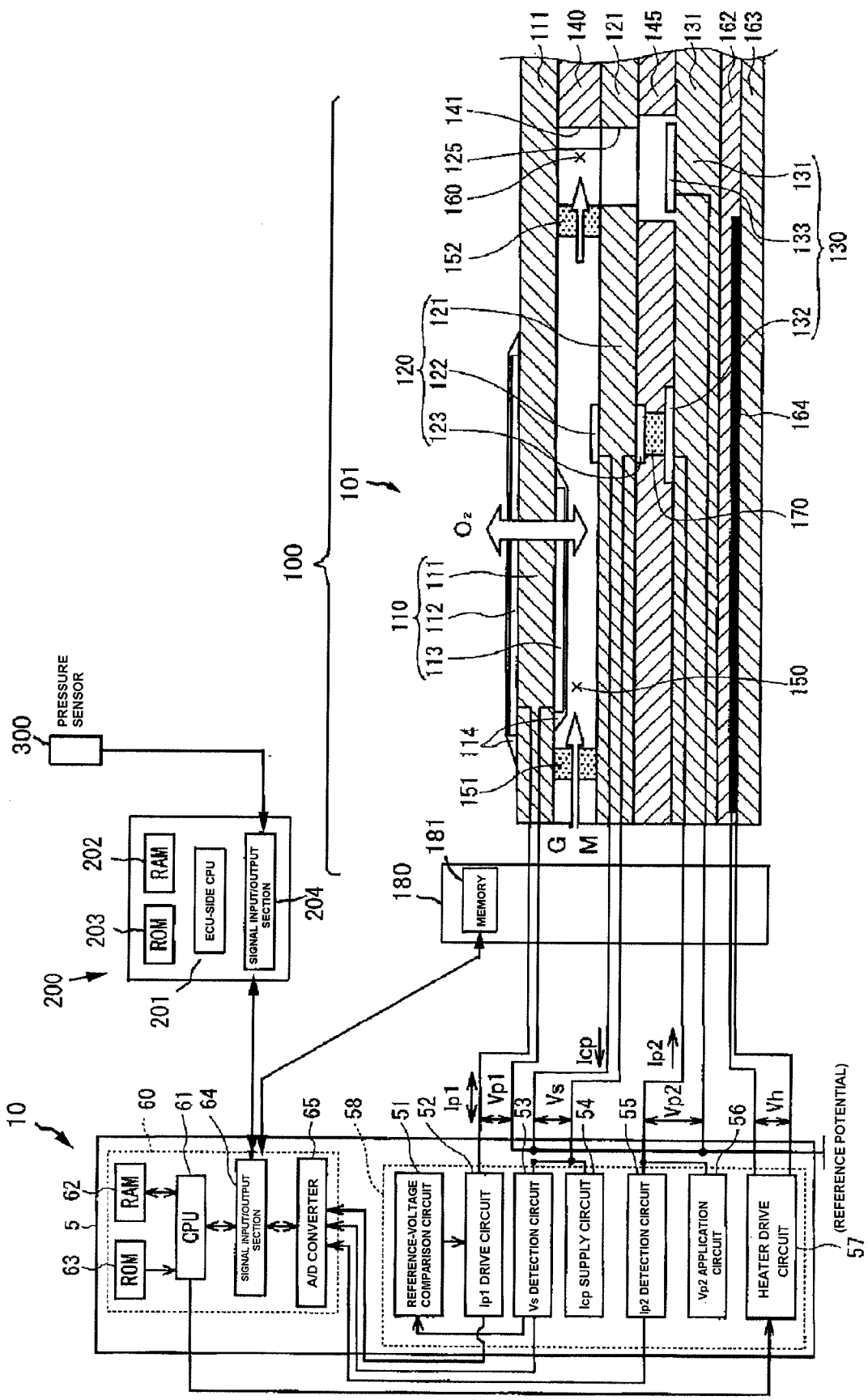
FIG. 1 is a block diagram showing the configuration of an $NO_X$ sensor control apparatus according to a first embodiment of the present invention.

Reference numerals used to identify various features in the drawings including the following.
10: $NO_X$ sensor control apparatus
52: Ip1 drive circuit (first pumping current detection circuit)
55: Ip2 detection circuit (second pumping current detection circuit)
60: microcomputer (oxygen concentration calculation unit; $NO_X$ concentration calculation unit)
100: $NO_X$ sensor
110: first pumping cell
112, 113: first electrode
130: second pumping cell
150: first measurement chamber
160: $NO_X$ measurement chamber
181: semiconductor memory (storage)
200: vehicle control apparatus
201: vehicle-side CPU (oxygen concentration calculation unit; $NO_X$ concentration calculation unit)
204: receiving unit (signal input/output section)
GM: to-be-measured gas
Ip1: first pumping current
Ip2: second pumping current

DETAILED DESCRIPTION OF THE PREFERRED EMBODIMENTS

Preferred embodiments of the present invention will next be described in detail by reference to the drawings. However, the present invention should not be construed as being limited thereto.

FIG. 1 is a block diagram showing the configuration of an $NO_X$ sensor control apparatus (an $NO_X$ detection apparatus) 10 according to a first embodiment of the present invention. In this embodiment, the $NO_X$ detection apparatus 10 corrects both oxygen concentration and $NO_X$ concentration values in accordance with the pressure of the exhaust gas.

The $NO_X$ detection apparatus 10 is mounted on a vehicle including an unillustrated internal combustion engine (hereinafter also referred to as an "engine"), and is electrically connected to a connector 180 of an $NO_X$ sensor 100. A semiconductor memory (storage) 181, such as ROM or the like, is incorporated into the connector 180 so as to store various coefficients (to be described later) set for an individual sensor 100.

Further, the $NO_X$ detection apparatus 10 is electrically connected to a vehicle control apparatus (hereinafter also referred to as an "ECU") 200.

The ECU 200 receives data representing oxygen concentration and $NO_X$ concentration of an exhaust gas which has been corrected by the $NO_X$ detection apparatus 10, and executes processing for controlling the operation state of the engine, processing for removing $NO_X$ accumulated in catalyst, and other processing on the basis of the received data. Further, the ECU 200 acquires from a pressure sensor 300 information of exhaust gas flowing through an exhaust pipe, and sends the information to the $NO_X$ detection apparatus 10. Notably, the method of acquiring the information regarding pressure of the exhaust gas is not limited to acquiring it from the pressure sensor 300. For example, the ECU 200 can read engine speed and engine load, and thereby determine the pressure of the exhaust gas therefrom using a map or calculation equation previously stored in ROM 203.

The ECU 200 includes an ECU-side CPU (central processing unit) 201, RAM 202, the ROM 203, a signal input/output section 204, and an unillustrated clock generator. Programs stored in the ROM 203 or the like in advance are executed by the CPU 201.

The $NO_X$ detection apparatus 10 includes a control circuit 58 and a microcomputer 60 provided on a circuit board. The microcomputer 60, which controls the entirety of the $NO_X$ detection apparatus 10, includes a CPU (central processing unit) 61, RAM 62, ROM 63, a signal input/output section 64, an A/D converter 65, and an unillustrated clock generator. Programs stored in the ROM 63 or the like in advance are executed by the CPU 61.

The control circuit 58 includes a reference-voltage comparison circuit 51, an Ip1 drive circuit 52, a Vs detection circuit 53, an Icp supply circuit 54, an Ip2 detection circuit 55, a Vp2 application circuit 56, and a heater drive circuit 57, which will be described in detail below. The control circuit 58 controls the $NO_X$ sensor 100, detects first and second pumping currents flowing through the $NO_X$ sensor 100, and outputs the detected first and second pumping currents to the microcomputer 60.

Notably, the microcomputer 60 and the Ip1 drive circuit 52 corresponds to the "first pumping current detector" of the present invention, and the microcomputer 60 and the Ip2 detection circuit 55 correspond to the "second pumping current detector" of the present invention. Further, the microcomputer 60 corresponds to the "oxygen concentration calculation unit" and the "$NO_X$ concentration calculation unit" of the present invention.

Next, the configuration of the $NO_X$ sensor 100 will be described. The $NO_X$ sensor 100 includes an $NO_X$ sensor element 101; a housing which accommodates the element 101; the above-mentioned connector 180 for connecting the element 101 and the $NO_X$ detection apparatus 10; and a lead wire connected to the element 101. Since the structure of the sensor itself is known, only the $NO_X$ sensor element 101 will be described below with reference to a longitudinal cross sectional view shown in FIG. 1.

The $NO_X$ sensor element 101 has a layered structure formed by stacking a first solid electrolyte layer 111, an insulation layer 140, a second solid electrolyte layer 121, an insulation layer 145, a third solid electrolyte layer 131, and insulation layers 162 and 163 in this order. A first measurement chamber 150 is defined between the first electrolyte layer 111 and the second electrolyte layer 121. A to-be-measured gas GM is introduced from the outside into first measurement chamber 150 via a first diffusion resistor 151 disposed at the left end (inlet) of the first measurement chamber 150.

A second diffusion resistor 152 is disposed at the end of the first measurement chamber 150 opposite the inlet. A second measurement chamber 160 (corresponding to the "$NO_X$ measurement chamber" of the present invention) is defined on the right side of the first measurement chamber 150, and communicates therewith via the second diffusion resistor 152. The second measurement chamber 160 is formed between the first electrolyte layer 111 and the third electrolyte layer 131 such that the second measurement chamber 160 penetrates through the second electrolyte layer 121.

An elongated plate-shaped heater 164, which extends along the longitudinal direction of the $NO_X$ sensor element 101, is embedded between the insulation layers 162 and 163. The heater 164 is used to heat the $NO_X$ sensor to an activation temperature so as to increase oxygen-ion conductivity of the solid electrolyte layer and thereby stabilize operation of the element.

The insulation layers 140 and 145 are formed mainly of alumina, and the first and second diffusion resistors 151 and 152 are formed of a porous material such as alumina. Further, the heater 164 is formed of platinum or the like.

A first pumping cell 110 includes the first solid electrolyte layer 111, which is formed mainly of zirconia having oxygen-ion conductivity; and paired inside and outside first pumping electrodes 113 and 112 disposed to sandwich the first solid electrolyte layer 111. The inner first pumping electrode 113 faces the first measurement chamber 150. Each of the inner and outer first pumping electrodes 113 and 112 is formed mainly of platinum; and the surface of each electrode is covered by a porous protection layer 114.

An oxygen concentration detection cell 120 includes the second solid electrolyte layer 121, which is formed mainly of zirconia; and a detection electrode 122 and a reference electrode 123 disposed to sandwich the second solid electrolyte layer 121. The detection electrode 122 faces the first measurement chamber 150 at a location downstream of the inner first pumping electrode 113. Each of the detection electrode 122 and the reference electrode 123 is formed mainly of platinum.

Notably, the insulation layer 145 is cut to form a cut-out portion such that the reference electrode 123 in contact with the second solid electrolyte layer 121 is disposed in the cut-out portion; and the cut-out portion is filled with a porous member, whereby a reference oxygen chamber 170 is formed. A constant weak current is supplied in advance to the oxygen concentration detection cell 120 by use of the Icp supply circuit 54, whereby oxygen is supplied from the first measurement chamber 150 to the reference oxygen chamber 170 so as to establish an oxygen reference.

A second pumping cell 130 includes the third solid electrolyte layer 131, which is formed mainly of zirconia; an inner second pumping electrode 133 disposed on a surface region of the third solid electrolyte layer 131, which surface region faces the second measurement chamber 160; and a counterpart second pumping electrode 132, which forms a pair together with the inner second pumping electrode 133. Each of the inner second pumping electrode 133 and the counterpart second pumping electrode 132 is formed mainly of platinum.

Notably, the counterpart second pumping electrode 132 is disposed on the third solid electrolyte layer 131 at a location corresponding to the cut-out portion of the insulation layer 145, so that the counterpart second pumping electrode 132 faces the reference electrode 123 via the reference oxygen chamber 170.

The inner first pumping electrode 113, the detection electrode 122, and the inner second pumping electrode 133 are connected to a reference potential. The outer first pumping electrode 112 is connected to the Ip1 drive circuit 52, and the reference electrode 123 is connected to the Vs detection circuit 53 and the Icp supply circuit 54 in parallel. Further, the counterpart second pumping electrode 132 is connected to the Ip2 detection circuit 55 and the Vp2 application circuit 56 in parallel. The heater drive circuit 57 is connected to the heater 164.

The various circuits mentioned above in the control circuit 58 have the functions described below.

The Ip1 drive circuit 52 supplies a first pumping current Ip1 between the inner first pumping electrode 113 and the outer first pumping electrode 112, while detecting the first pumping current Ip1.

The Vs detection circuit 53 detects a voltage Vs between the detection electrode 122 and the reference electrode 123, and outputs the detected voltage to the reference-voltage comparison circuit 51.

The reference-voltage comparison circuit 51 compares a reference voltage (e.g., 425 mV) and the output of the Vs detection circuit 53, and outputs a comparison result to the Ip1 drive circuit 52. The Ip1 drive circuit 52 controls the Ip1 current such that the voltage Vs becomes equal to the reference voltage, to thereby adjust the oxygen concentration in the first measurement chamber 150 to a level at which $NO_X$ does not decompose.

The Icp supply circuit 54 causes a weak current Icp to flow between the detection electrode 122 and the reference electrode 123 so as to supply oxygen from the first measurement chamber 150 into the reference oxygen chamber 170, to thereby expose the reference electrode 123 to a predetermined oxygen concentration, which serves as a reference.

The Vp2 application circuit 56 applies a constant voltage Vp2 (e.g., 450 mV) between the inner second pumping electrode 133 and the counterpart second pumping electrode 132, the voltage being determined such that the $NO_X$ gas within the to-be-measured gas GM is decomposed into oxygen and $N_2$ gas. Thus, the $NO_X$ is decomposed into nitrogen and oxygen.

The Ip2 detection circuit 55 detects a second pumping current Ip2 which flows through the second pumping cell 130 so as to pump out of the second measurement chamber 160 the oxygen produced as a result of the decomposition of $NO_X$.

The Ip1 drive circuit 52 outputs the detected value of the first pumping current Ip1 to the A/D converter 65. Further, the Ip2 detection circuit 55 outputs the detected value of the second pumping current Ip2 to the A/D converter 65.

The A/D converter 65 converts these values to digital values, and outputs them to the CPU 61 via the signal input/output section 64.

Next, an example of control of the $NO_X$ sensor 100 performed by the control circuit 58 will be described. First, when electrical power is supplied from an external power supply upon startup of the engine, the heater 164 is activated via the heater circuit 57 so as to heat the first pumping cell 110, the oxygen concentration detection cell 120, and the second pumping cell 130 to the activation temperature. Further, the Icp supply circuit 54 causes a weak current Icp to flow between the detection electrode 122 and the reference electrode 123, so as to supply oxygen from the first measurement chamber 150 into the reference oxygen chamber 170 for use as a reference.

Once heating of the cells 110 to 130 to the activation temperature is complete, the first pumping cell 110 pumps oxygen out of the to-be-measured gas (exhaust gas) GM having flowed into the first measurement chamber 150, whereby oxygen flows from the inner first pumping electrode 113 to the outer first pumping electrode 112.

At that time, the oxygen concentration within the first chamber 150 corresponds to the inter-electrode voltage (inter-terminal voltage) Vs of the oxygen concentration detection cell 120. Therefore, the Ip1 drive circuit 52 controls the first pumping current Ip1, which flows through the first pumping cell 110. In this manner, the inter-electrode voltage Vs becomes equal to the above-described reference voltage, to thereby adjust the oxygen concentration within the first measurement chamber 150 to a level at which $NO_X$ does not decompose.

The to-be-measured gas GM having the adjusted oxygen concentration further flows toward the second measurement chamber 160. The Vp2 application circuit 56 applies, as the inter-electrode voltage (inter-terminal voltage) of the second pumping cell 130, a constant voltage Vp2 determined such that $NO_X$ gas within the to-be-measured gas GM is decomposed into oxygen and $N_2$ gas (a voltage, e.g., 450 mV), the constant voltage Vp2 being higher than the value of the control voltage of the oxygen concentration detection cell 120. Thus, the second pumping current Ip2 flows through the second pumping cell 130 such that the oxygen produced as a result of the decomposition of the $NO_X$ is pumped out from the second chamber 160. Since a linear relation exists between the second pumping current Ip2 and the $NO_X$ concentration, the $NO_X$ concentration within the to-be-measured gas can be detected from the second pumping current Ip2 detected by the Ip2 detection circuit 55.

As described above, the $NO_X$ sensor 100 introduces the to-be-measured gas GM from the outside via the first diffusion resistor 151. Therefore, the amount of gas flowing into the first measurement chamber 150 and the second measurement chamber 160 changes in accordance with a change in pressure of the to-be-measured gas GM around the sensor. If the amount of gas inflow changes, the respective pumping currents of the first pumping cell 110 and the second pumping cell 130 change, and if pressure correction as employed in the first embodiment of the present invention is not performed, the oxygen concentration and $NO_X$ concentration thus calculated will change.

Figure 2:
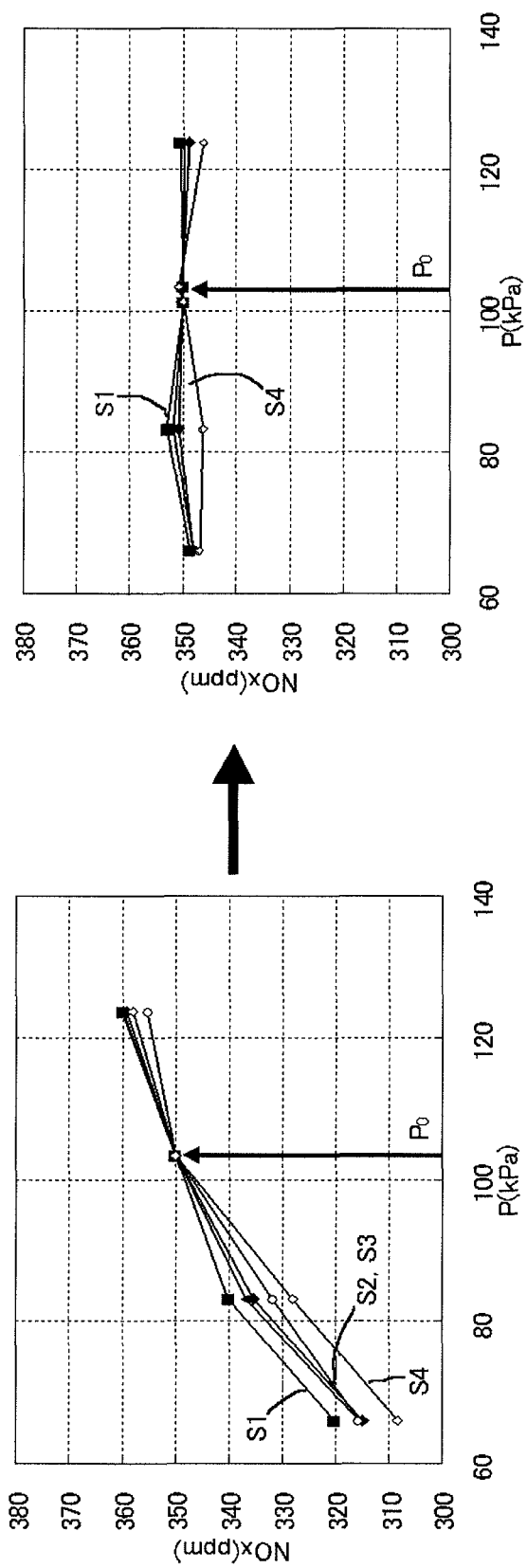
FIG. 2 has two graphs each showing a change in $NO_X$ concentration (sensor output) observed when the pressure of a to-be-measured gas is changed. The graph on the left shows correction at a reference pressure $P_0$ for sensors S1 to S4. The graph on the right shows further compensation by use of $NO_X$ pressure correction information set for each individual sensor.

The graphs of FIG. 2 show the change in $NO_X$ concentration with a change in pressure of the to-be-measured gas GM around the $NO_X$ sensor. The change in $NO_X$ concentration was determined, in accordance with a predetermined calculation equation, from a change in the second pumping current Ip2 detected when the pressure of the to-be-measured gas GM was changed. FIG. 2 shows that when the pressure of the to-be-measured gas GM changes, the calculated value of the $NO_X$ concentration changes even when the same $NO_X$ sensor is used.

Further, since the diffusion resistance of the first diffusion resistor 151 varies among $NO_X$ sensors due to production variations, even when the pressure of the to-be-measured gas GM is the same, relatively large differences are produced among the $NO_X$ concentrations calculated from the outputs of $NO_X$ sensors S1 to S4 as shown in the left graph of FIG. 2. In the case of the left graph of FIG. 2, the variation of the diffusion resistance of the first diffusion resistor 151 is corrected such that the $NO_X$ concentrations calculated from the outputs of $NO_X$ sensors S1 to S4 become the same only at a reference pressure (atmospheric pressure Po; the arrow shown in FIG. 2). Therefore, at the reference pressure, the $NO_X$ concentrations calculated from the outputs of $NO_X$ sensors S1 to S4 assume the same value.

If the change in $NO_X$ concentration with pressure is uniformly corrected (the same correction equation or correction amount is applied to the individual $NO_X$ sensors), the $NO_X$ concentrations calculated from the outputs of these $NO_X$ sensors do not become the same. This is because production variations among the individual $NO_X$ sensors are not taken into consideration.

In view of the above, in the first embodiment, the change in $NO_X$ concentration with pressure is compensated by use of $NO_X$ pressure correction information (second pressure correction information) set for each individual $NO_X$ sensor and information regarding the pressure of the to-be-measured gas GM obtained from the pressure sensor 300 This compensation corrects for variation in the second pumping current Ip2 (that is, the calculated $NO_X$ concentration value) attributable to production variation in the individual $NO_X$ sensors, and corrects for variation in the calculated $NO_X$ concentration attributable to a change in the pressure of the to-be-measured gas GM. This correction suppresses deviation in the calculated $NO_X$ concentration value due to production variation of the individual $NO_X$ sensors and the change in the pressure of the to-be-measured gas GM, which deviation would otherwise occur even when the $NO_X$ concentration remains unchanged (the right graph of FIG. 2). In this manner, the $NO_X$ concentration can be detected accurately.

Pressure correction is similarly performed for the oxygen concentration calculated (converted) from the first pumping current in accordance with a predetermined calculation equation. That is, oxygen pressure correction information (first pressure correction information) is set for each individual $NO_X$ sensor, and the pressure correction is performed by use of this oxygen pressure correction information and the information regarding the pressure of the to-be-measured gas GM obtained from the pressure sensor 300.

In the $NO_X$ sensor control apparatus 10 according to the first embodiment of the present invention, the pressure correction for the $NO_X$ concentration is performed in accordance with the following Equation 1, where $NO_{XP}$ represents $NO_X$ concentration ($NO_X$ concentration value calculated from the second pumping current) before pressure correction (hereinafter also referred to as the "uncorrected $NO_X$ concentration") at pressure P; $NO_{XPo}$ represents $NO_X$ concentration ($NO_X$ concentration value) after pressure correction (hereinafter also referred to as the "corrected $NO_X$ concentration") at pressure Po; P represents the pressure (kPa) of the to-be-measured gas; Po represents atmospheric pressure (=101.3 kPa); and $k_1$ represents an $NO_X$ pressure correction coefficient (second pressure correction information).

$$NO_{X_{P_o}} = NO_{XP}\left(\frac{k_1 + P}{P}\right)\left(\frac{P_o}{k_1 + P_0}\right) \quad (1)$$

However, the method for pressure correction is not limited to use of a function such as Equation 1, and a map in which a correction amount is assigned to each of pressure ranges may be used in place of an equation.

Notably, since the second pumping current Ip2 has a fixed relation with the $NO_X$ concentration within the to-be-measured gas, the uncorrected $NO_X$ concentration $NO_{XP}$ at pressure P can be calculated from the second pumping current Ip2. The microcomputer 60 performs this calculation by reading out of ROM 63 an equation representing the relation between Ip2 and the $NO_X$ concentration in the to-be-measured gas.

The $NO_X$ pressure correction coefficient ($k_1$) is selected from a map shown in FIG. 3. A value of $k_1$ corresponding to a rank assigned to the $NO_X$ sensor (i.e., a rank assigned to an individual $NO_X$ sensor) is set as the $NO_X$ pressure correction coefficient for the $NO_X$ sensor. Notably, each individual gas sensor control apparatus is assigned only one of the above-described correction ranks. In this case, before the gas sensor control apparatus is shipped, the map of FIG. 3 is previously stored in the semiconductor memory 181 associated with the individual $NO_X$ sensors. Each $NO_X$ sensor is connected to an external testing device, and an $NO_X$ concentration value is calculated from the second pumping current Ip2 in a state in which a reference gas is used and the gas pressure is selectively set to a plurality of known gas pressures, whereby the value of $k_1$ is determined. For example, in the case where the $NO_X$ concentration is measured at two points, the slope of a straight line is set as the value of $k_1$. Subsequently, a rank shown in the map of FIG. 3 whose value of $k_1$ is closest to the slope is determined, and is assigned to the $NO_X$ sensor. For example, a flag indicating the rank is set in the map. Thus, only data corresponding to a single correction rank within the map are referred to. Notably, a gas containing NO (90 ppm), $H_2O$ (3 vol %), $O_2$ (9 vol %), and $N_2$ (balance) was used as the reference gas. In this manner, the value of $k_1$ for each individual $NO_X$ sensor is stored in the semiconductor memory 181.

Notably, in the case where measurement is performed at three or more known pressures, the value of $k_1$ may be set as a predetermined curve or a map in which a coefficient is assigned to each pressure range.

In the $NO_X$ sensor control apparatus 10 according to the first embodiment of the present invention, the pressure correction for the oxygen concentration is performed in accordance with the following Equation 2, wherein $O_P$ represents oxygen concentration (oxygen concentration value calculated from the first pumping current) before pressure correction (hereinafter also referred to as the "uncorrected oxygen concentration") at pressure P; $O_{Po}$ represents oxygen concentration (oxygen concentration value) after pressure correction (hereinafter also referred to as the "corrected oxygen concentration") at pressure Po; P represents the pressure (kPa) of the to-be-measured gas; Po represents atmospheric pressure (=101.3 kPa); and $k_2$ represents an oxygen pressure correction coefficient (oxygen pressure correction information).

$$O_{P_o} = O_P\left(\frac{k_2 + P}{P}\right)\left(\frac{P_o}{k_2 + P_0}\right) \quad (2)$$

Notably, since the first pumping current Ip1 has a fixed relation with the oxygen concentration in the to-be-measured gas, the uncorrected oxygen concentration $O_P$ at the pressure P can be calculated from the first pumping current Ip1. The microcomputer 60 performs this calculation by reading out of ROM 63 an equation representing the relation between the first pumping current Ip1 and the oxygen concentration in the to-be-measured gas.

The oxygen pressure correction coefficient ($k_2$) is selected from a map similar to that shown in FIG. 3. A value of $k_2$ corresponding to a rank assigned to the individual $NO_X$ sensor is set as the oxygen pressure correction coefficient for the $NO_X$ sensor. Thus, a selected value of $k_2$ is stored in the semiconductor memory 181. Similar to the above-described $k_1$, the value of $k_2$ is determined by connecting each $NO_X$ sensor to an external testing device, and calculating an oxygen concentration value from the first pumping current Ip1 in a state in which a reference gas is used and the gas pressure is selectively set to a plurality of known gas pressures.

Next, a pressure correction processing flow in the $NO_X$ sensor control apparatus 10 according to the first embodiment of the present invention will be described with reference to FIG. 4. Notably, the oxygen concentration calculation unit and the $NO_X$ concentration calculation unit of the present invention will both be described as operations of the microcomputer 60 without being separately described.

First, the microcomputer 60 accesses the semiconductor memory 181 mounted on the connector 180 of the $NO_X$ sensor 100, and acquires the oxygen pressure correction coefficient ($k_2$) from the semiconductor memory 181 (step S2). Similarly, the microcomputer 60 accesses the semiconductor memory 181, and acquires the $NO_X$ pressure correction coefficient ($k_1$) from the semiconductor memory 181 (step S4).

Further, the microcomputer 60 acquires the pressure of the to-be-measured gas (pressure information) via the ECU 200 (step S6).

Subsequently, the microcomputer 60 performs the processing of a main loop (step S8). First, the microcomputer 60 acquires a value of the first pumping current Ip1 from the Ip1 drive circuit 52 (specifically, a detection signal generated through voltage conversion of the first pumping current Ip1) (step S10).

The microcomputer 60 then reads out of ROM 63 an equation representing the relation between the first pumping current Ip1 and the oxygen concentration of the to-be-measured gas, and calculates the uncorrected oxygen concentration (the oxygen concentration value) $O_P$ (step S11).

Next, the microcomputer 60 applies the oxygen pressure correction coefficient ($k_2$) and the pressure of the to-be-measured gas obtained in steps S2 and S6 to Equation 2 so as to calculate the corrected oxygen concentration $O_{Po}$ (step S12).

Here, the corrected oxygen concentration $O_{Po}$ is a value at the pressure Po (atmospheric pressure).

The microcomputer 60 then outputs (transmits) the calculated oxygen concentration $O_{Po}$ to the ECU 200 via the signal input/output section 64 (step S14).

Similarly, the microcomputer 60 acquires a value of the second pumping current Ip2 from the Ip2 detection circuit 55 (specifically, a detection signal generated through voltage conversion of the second pumping current Ip2) (step S18).

The microcomputer 60 then reads out of ROM 63 an equation representing the relation between the second pumping current Ip2 and the $NO_X$ concentration of the to-be-measured gas, and calculates the uncorrected $NO_X$ concentration (the $NO_X$ concentration value) $NO_{XP}$ (step S19).

Next, the microcomputer 60 applies the $NO_X$ pressure correction coefficient ($k_1$) and the pressure of the to-be-measured gas obtained in steps S4 and S6 to Equation 1 so as to calculate the corrected $NO_X$ concentration $NO_{XP0}$ (step S20). Here, $NO_{XP0}$ is a value at the pressure Po (atmospheric pressure).

The microcomputer 60 then outputs (transmits) the calculated $NO_X$ concentration $NO_{XP0}$ to the ECU 200 via the signal input/output section 64 (step S22).

The microcomputer 60 determines in step S26 whether to end the processing. When the processing is to be continued, the microcomputer 60 returns to step S8.

As described above, according to the first embodiment, the $NO_X$ concentration information and the oxygen concentration information (specifically, the $NO_X$ concentration value and the oxygen concentration value) can be corrected in accordance with the pressure of the to-be-measured gas. Further, in the case where the pressure dependencies of the $NO_X$ concentration information and the oxygen concentration information are previously measured for each individual $NO_X$ sensor and the measured pressure dependencies are stored as an oxygen pressure correction coefficient and an $NO_X$ pressure correction coefficient, the pressure dependency of the concentration information which varies among the individual sensors can be reflected in the correction. In this manner, the $NO_X$ concentration and the oxygen concentration can be determined using a single $NO_X$ sensor irrespective of a change in pressure of the to-be-measured gas.

Further, in the case where the oxygen pressure correction coefficient ($k_2$) and the $NO_X$ pressure correction coefficient ($k_1$) are stored on the $NO_X$ sensor side (in the semiconductor memory thereof), processing to store the values of the oxygen pressure correction coefficient and the $NO_X$ pressure correction coefficient in the $NO_X$ sensor control apparatus is unnecessary. Since the oxygen pressure correction coefficient ($k_2$) and the $NO_X$ pressure correction coefficient ($k_1$) are stored in the semiconductor memory on the $NO_X$ sensor side at the time of shipment inspection of the $NO_X$ sensor, these coefficients need not be measured separately, so that the working load is reduced.

Next, an $NO_X$ sensor control apparatus according to a second embodiment of the present invention will be described. The $NO_X$ sensor control apparatus according to the second embodiment is identical to the first embodiment, except that the processing of microcomputer 60 differs from that of the first embodiment.

Figure 5A:
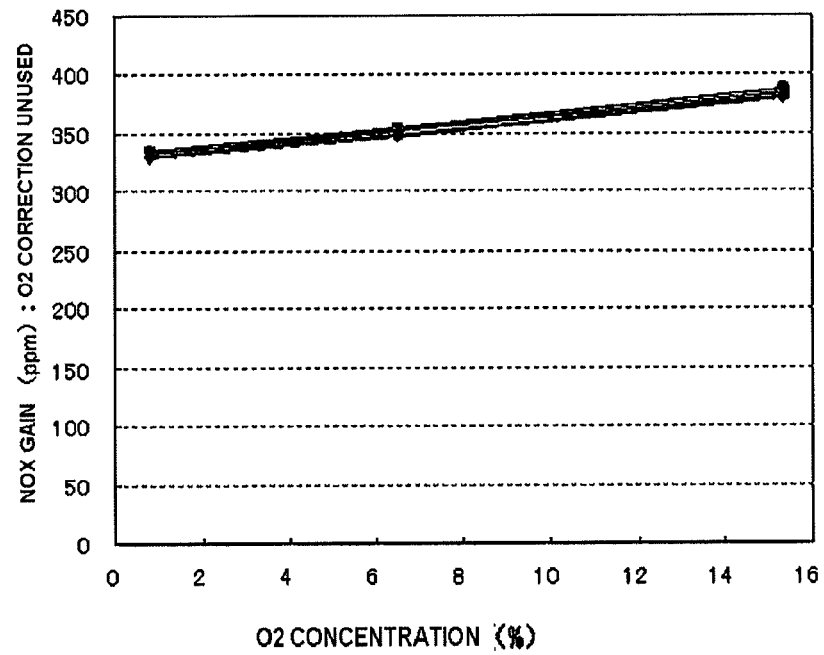
FIGS. 5(a) and 5(b) are graphs showing a relation equation for calculating $NO_X$ concentration from Ip2.

Incidentally, in the case of the $NO_X$ sensor of the first embodiment, even when the $NO_X$ concentration in the to-be-measured gas and the pressure thereof are constant, if the oxygen concentration within the to-be-measured gas changes, the second pumping current Ip2 changes accordingly. That is, the calculated $NO_X$ concentration has an oxygen concentration dependency (FIG. 5(a)). Therefore, in order to improve the detection accuracy of the $NO_X$ concentration, correction is desirably performed in consideration of oxygen concentration dependency as well as the above-described pressure dependency.

One possible way is to correct the $NO_X$ concentration value, obtained in accordance with the above-described Equation 1, using the uncorrected oxygen concentration value obtained from the first pumping current Ip1. However, since the uncorrected oxygen concentration value itself is influenced by a change in the pressure of the to-be-measured gas, accurate correction of the oxygen concentration dependency is not always carried out.

Figure 5B:
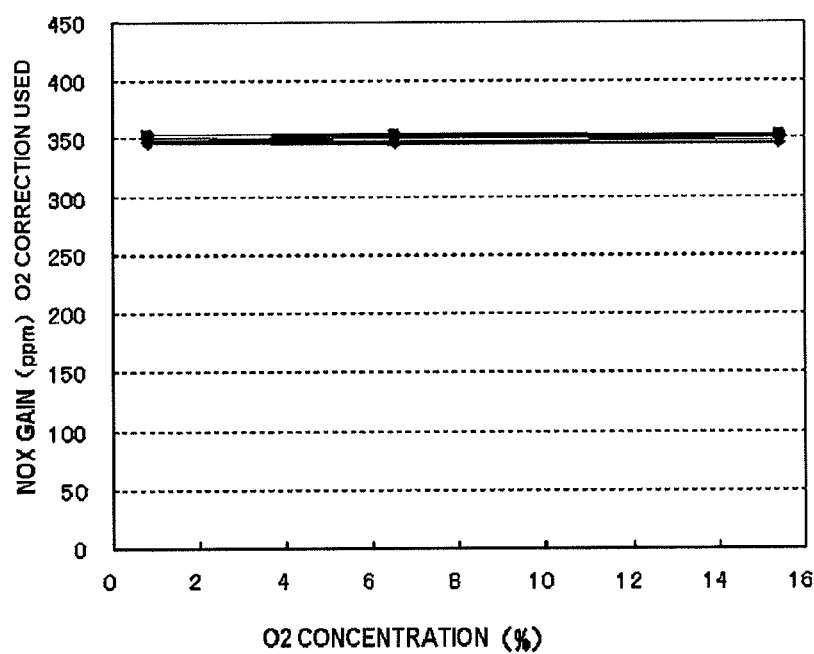

In view of the above, in the second embodiment, when the $NO_X$ concentration value is corrected using the oxygen concentration value, the oxygen concentration value is not simply calculated from the first oxygen pumping current Ip1. Rather, the oxygen concentration value is calculated using the above-described Equation 2 in which the oxygen pressure correction information and the pressure of the to-be-measured gas GM are taken into consideration, whereby the $NO_X$ concentration value is corrected using the corrected oxygen concentration $O_{Po}$. Notably, for the correction, oxygen concentration dependency at a predetermined gas pressure is previously obtained for each individual $NO_X$ sensor (see FIG. 5(a)); a correction equation in which the dependency is taken into consideration or a map in which a correction amount is set in accordance with oxygen concentration is prepared; and the correction equation or the map is stored in the microcomputer. Then, the corrected oxygen concentration $O_{Po}$ is applied to the above-described relation equation or the map to thereby correct the $NO_X$ concentration value. Thus, it becomes possible to effectively prevent the $NO_X$ concentration value from changing with a change in oxygen concentration of the to-be-measured gas as shown in FIG. 5(b).

Figure 6:
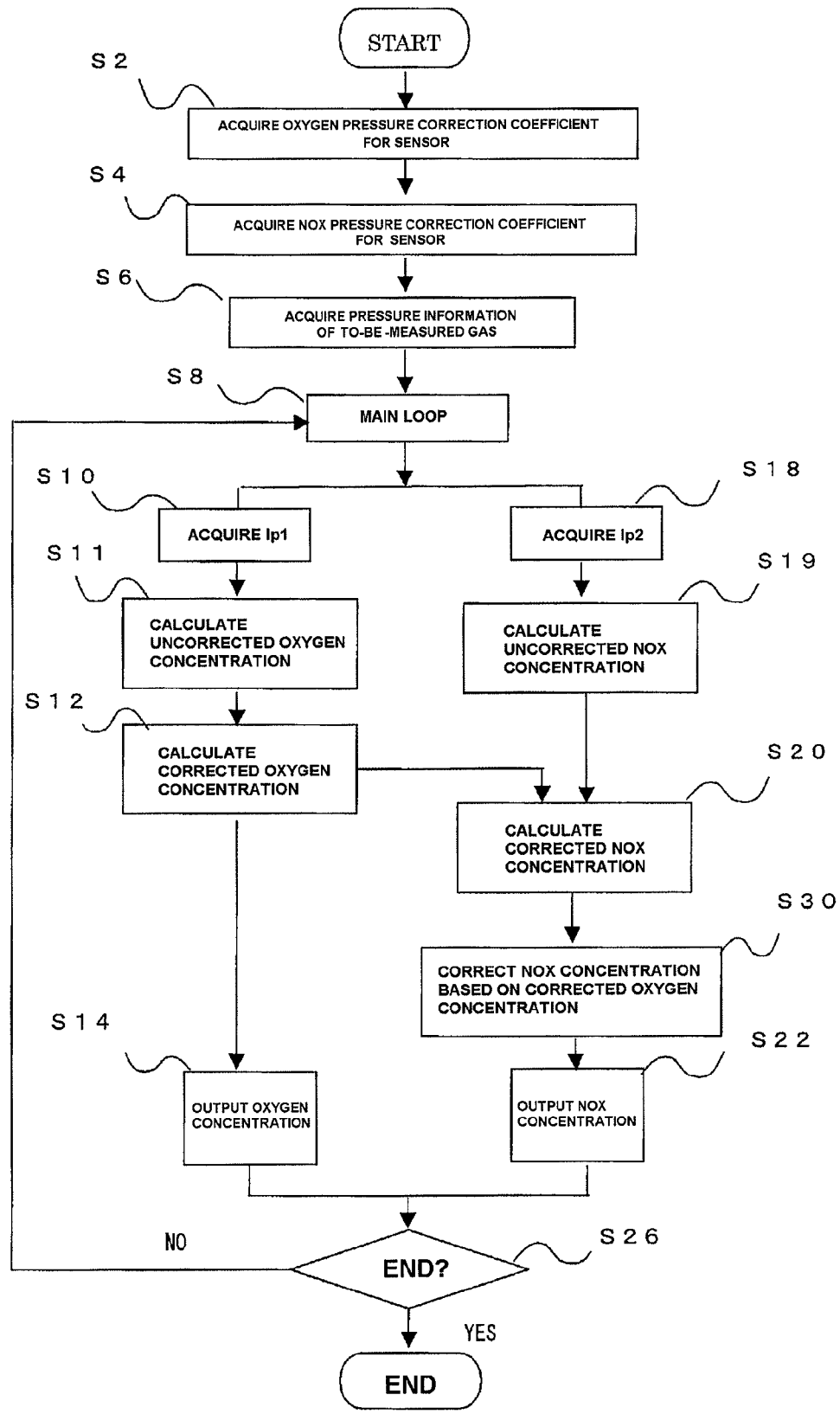
FIG. 6 is a chart showing a pressure correction processing sequence in the $NO_X$ sensor control apparatus according to a second embodiment of the present invention.

FIG. 6 shows the pressure correction processing flow in the $NO_X$ sensor control apparatus according to a second embodiment of the invention. Notably, processing steps identical with those of the first embodiment are denoted by the same step numbers as shown in FIG. 4, and their descriptions will not be repeated.

Figure 4:
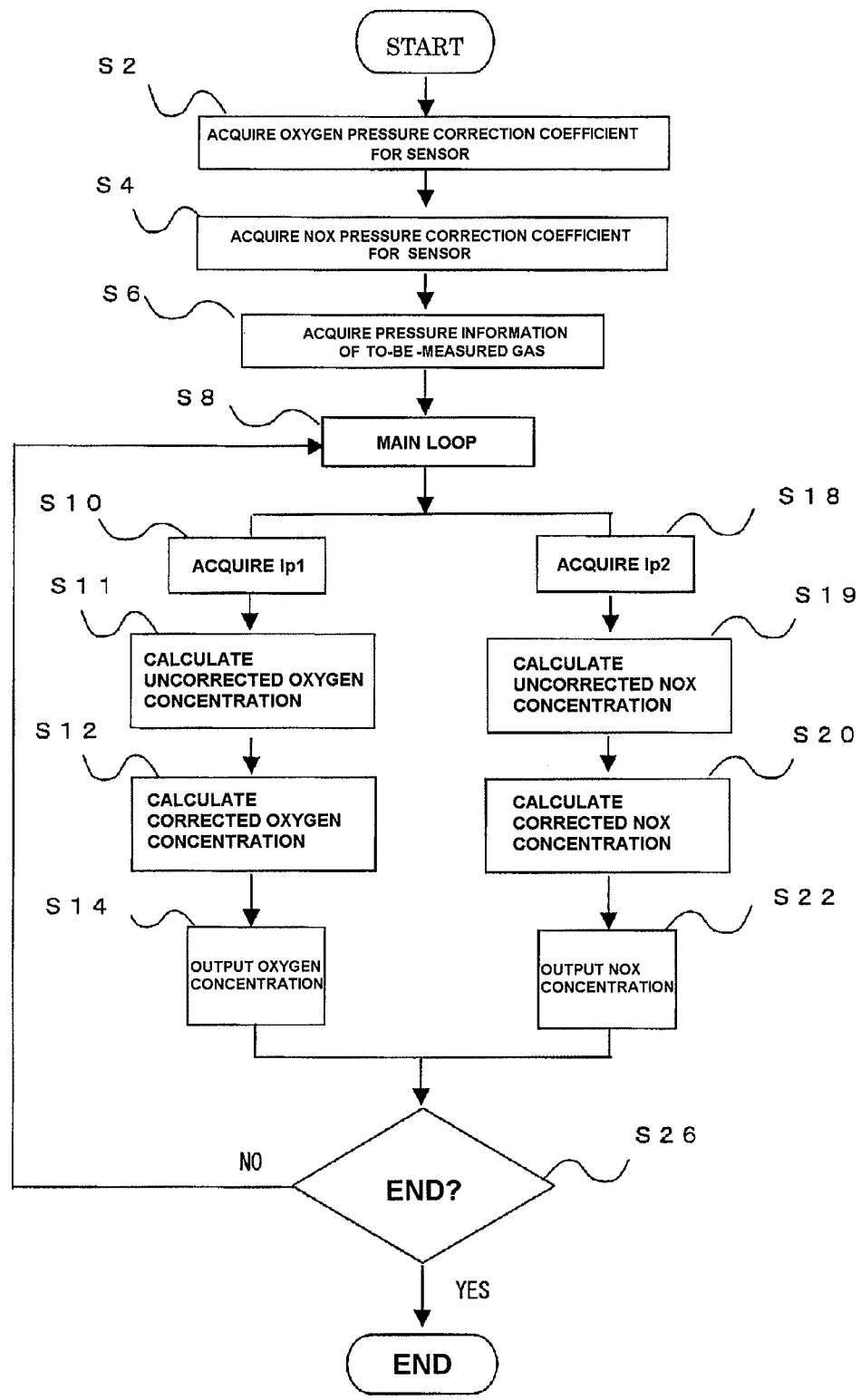
FIG. 4 is a chart showing a pressure correction processing sequence in the $NO_X$ sensor control apparatus according to the first embodiment of the present invention.

The second embodiment is identical to the first embodiment, except that a new step S30 is added between steps S20 and S22 of FIG. 4. In step S30, the microcomputer 60 corrects the corrected $NO_{XP0}$ using the above-described relation equation or the map stored in the microcomputer, while using the corrected oxygen concentration $O_{Po}$ obtained in step S12. Then, in step 22, the microcomputer 60 outputs (sends) the corrected $NO_{XP0}$, which has been corrected for oxygen concentration dependency, to the ECU 200 via the signal input/output section 64.

In the case of the second embodiment, since the corrected $NO_{XP0}$ is corrected using the corrected oxygen concentration $O_{Po}$, a more accurate $NO_X$ concentration value can be obtained with reduced influence of a change in the pressure of the to-be-measured gas and a change in oxygen concentration of the to-be-measured gas.

Notably, the method of calculating the oxygen concentration from the first pumping current Ip1, the method of calculating the $NO_X$ concentration from the second pumping current Ip2, and the configuration and circuit arrangement of the control circuit 58 of the $NO_X$ detection apparatus 10 (other than the pressure correction), which are employed in the embodiments of the present invention, are similar to those disclosed in US Patent Application Publication numbers US 2002/0017467 and US 2002/0162743, incorporated herein by reference.

Next, the vehicle control apparatus according to a third embodiment of the invention will be described. This embodiment is identical to the above-described first and second embodiments, except that the processing for pressure correction is performed in the ECU (vehicle control apparatus) 200 rather than in the $NO_X$ sensor control apparatus. Therefore, description identical with those of the flowcharts (FIGS. 4 and 6) relating to the first and second embodiments is omitted. Since the ECU-side CPU 201 itself calculates the corrected oxygen concentration and the corrected $NO_X$ concentration, steps S14 and S22 in FIGS. 4 and 6 become unnecessary.

The signal input/output section 204 corresponds to the "receiving unit" of the present invention, and the ECU-side CPU 201 corresponds to the "oxygen concentration calculation unit" and the "$NO_X$ concentration calculation unit."

As used herein, "ECU-side" means within the ECU housing or package, or in its vicinity (e.g., physically located close to the ECU, perhaps residing in a connector electrically connected to the ECU, and closer to the ECU than to the $NO_X$ sensor control apparatus 10 or to the $NO_X$ sensor 100).

Next, in the case where the present embodiment is combined with first embodiment, the processing executed by the ECU-side CPU 201 will be described with reference to FIG. 4. Notably, even when the present embodiment is combined with the second embodiment, the ECU-side CPU 201 processing is performed in accordance with a sequence similar to that of FIG. 6. Therefore, a description of such a case is omitted.

First, the ECU-side CPU 201 accesses the semiconductor memory 181 via the microcomputer 60, and acquires the oxygen pressure correction coefficient ($k_2$) stored in the semiconductor memory 181 (step S2). Similarly, the ECU-side CPU 201 acquires the $NO_X$ pressure correction coefficient ($k_1$) from the semiconductor memory 181 (step S4).

Further, the ECU-side CPU 201 acquires the information regarding the pressure of the to-be-measured gas from the pressure sensor 300 (step S6).

Subsequently, the ECU-side CPU 201 performs the processing of a main loop (step S8). First, the ECU-side CPU 201 acquires a value of the first pumping current Ip1 from the Ip1 drive circuit 52 (more precisely, a detection signal generated through voltage conversion of the first pumping current Ip1) via the microcomputer 60 (step S10).

The ECU-side CPU 201 then reads out of ROM 63 an equation representing the relation between the first pumping current Ip1 and the oxygen concentration of the to-be-measured gas, and calculates the uncorrected oxygen concentration (the oxygen concentration value) $O_P$ (step S11).

Next, the ECU-side CPU 201 applies the oxygen pressure correction coefficient ($k_2$) and the pressure of the to-be-measured gas obtained in steps S2 and S6 to Equation 2 so as to calculate the corrected oxygen concentration $O_{P0}$ (step S12). Here, $O_{P0}$ is a value at the pressure Po (atmospheric pressure). Notably, since the first pumping current Ip1 has a fixed relation with the oxygen concentration in the to-be-measured gas, the uncorrected oxygen concentration $O_P$ at the pressure P can be calculated from the first pumping current Ip1. The ECU-side CPU 201 performs this calculation by reading out of a predetermined ROM an equation representing the relation between the first pumping current Ip1 and the oxygen concentration within the to-be-measured gas.

Similarly, the ECU-side CPU 201 acquires a value of the second pumping current Ip2 from the Ip2 detection circuit 55 (more precisely, a detection signal generated through voltage conversion of the second pumping current Ip2) via the microcomputer 60 (step S18).

The ECU-side CPU 201 then reads out of ROM an equation representing the relation between the second pumping current Ip2 and the $NO_X$ concentration, and calculates the uncorrected $NO_X$ concentration (the $NO_X$ concentration value) $NO_{XP}$ (step S19).

Next, the ECU-side CPU 201 applies the $NO_X$ pressure correction coefficient ($k_1$) and the pressure of the to-be-measured gas obtained in steps S4 and S6 to Equation 1 so as to calculate the corrected $NO_X$ concentration $NO_{XP0}$ (step S20). Here, $NO_{XP0}$ is a value at the pressure Po (atmospheric pressure). Notably, since the second pumping current Ip2 has a fixed relation with the $NO_X$ concentration in the to-be-measured gas, the uncorrected $NO_X$ concentration $NO_{XP}$ at the pressure P can be calculated from the second pumping current Ip2. The ECU-side CPU 201 performs this calculation by reading out of the predetermined ROM an equation representing the relation between the second pumping current Ip2 and the $NO_X$ concentration within the to-be-measured gas.

The ECU-side CPU 201 determines in step S26 whether to end the processing. When the processing is to be continued, the ECU-side CPU 201 returns to step S8.

Notably, steps S14 and S22 may be omitted from the sequences shown in FIGS. 4 and 6 in the case where the ECU-side CPU 201 is not required to output the oxygen concentration and the $NO_X$ concentration to an external unit.

It should further be apparent to those skilled in the art that various changes in form and detail of the invention as shown and described above may be made. It is intended that such changes be included within the spirit and scope of the claims appended hereto.

This application is based on Japanese Patent Application No. JP 2008-54432 filed Mar. 5, 2008, incorporated herein by reference in its entirety.

What is claimed is:

1. An $NO_x$ sensor control apparatus connectable to an $NO_x$ sensor, the $NO_x$ sensor comprising a first pumping cell which has paired first electrodes provided internally and externally, respectively, of a first measurement chamber and which pumps oxygen out of a to-be-measured gas introduced into the first measurement chamber or pumps oxygen into the first measurement chamber to thereby adjust oxygen concentration in the first measurement chamber; and a second pumping cell which has paired second electrodes provided internally and externally, respectively, of an $NO_x$ measurement chamber in communication with the first measurement chamber, the second pumping cell being configured such that a second pumping current flows between the paired second electrodes, the second pumping current corresponding to $NO_x$ concentration of the to-be-measured gas having flowed from the first measurement chamber into the $NO_x$ measurement chamber and having an adjusted oxygen concentration, the $NO_x$ sensor control apparatus comprising:

a first pumping current detector for detecting a first pumping current flowing between the paired first electrodes of the first pumping cell;

a second pumping current detector for detecting the second pumping current flowing between the paired second electrodes of the second pumping cell;

an oxygen concentration calculation unit programmed to calculate an oxygen concentration of the to-be-measured gas based on the first pumping current and programmed to correct the calculated oxygen concentration in accordance with the following equation:

$$O_{P_o} = O_P\left(\frac{k_2 + P}{P}\right)\left(\frac{P_o}{k_2 + P_0}\right)$$

where $O_p$ represents an oxygen concentration value calculated from the first pumping current before pressure correction at pressure P; $O_{po}$ represents oxygen concentration after pressure correction at pressure Po; P represents the pressure (kPa) of the to-be-measured gas; Po represents atmospheric pressure: and $k_2$ represents a predetermined oxygen pressure correction coefficient; and an $NO_x$ concentration calculation unit programmed to calculate an $NO_x$ concentration of the to-be-measured gas based on the second pumping current and programmed to correct the calculated $NO_x$ concentration in accordance with the following equation:

$$NO_{x_{P_o}} = NO_{x_P}\left(\frac{k_1 + P}{P}\right)\left(\frac{P_o}{k_1 + P_0}\right)$$

where $NO_{xp}$ represents a $NO_x$ concentration value calculated from the second pumping current before pressure correction at pressure P; $NO_{xpo}$ represents $NO_x$ concentration after pressure correction at pressure Po; P represents the pressure (kPa) of the to-be-measured gas; Po represents atmospheric pressure; and $K_1$ represents a predetermined $NO_x$ pressure correction coefficient, wherein the $NO_x$ concentration calculation unit is programmed to calculate the $NO_x$ concentration of the to-be-measured gas based on the second pumping current and corrected in accordance with the pressure of the to-be-measured gas, the predetermined $NO_x$ pressure correction coefficient, and the corrected oxygen concentration calculated by the oxygen concentration calculation unit.

2. The $NO_x$ sensor control apparatus according to claim 1, wherein the first pressure correction information and the second pressure correction information are stored in a storage unit associated with the $NO_x$ sensor.

3. A system including vehicle control apparatus, an $NO_x$ sensor control apparatus and $NO_x$ sensor, the vehicle control apparatus communicates with the $NO_x$ sensor control apparatus connectable to the $NO_x$ sensor, the system comprising the $NO_x$ sensor comprising a first pumping cell which has paired first electrodes provided internally and externally, respectively, of a first measurement chamber and which pumps oxygen out of a to-be-measured gas introduced into the first measurement chamber or pumps oxygen into the first measurement chamber to thereby adjust oxygen concentration in the first measurement chamber;

and a second pumping cell which has paired second electrodes provided internally and externally, respectively, of an $NO_x$ measurement chamber in communication with the first measurement chamber, the second pumping cell being configured such that a second pumping current flows between the paired second electrodes, the second current corresponding to $NO_x$ concentration of the to-be-measured gas having flowed from the first measurement chamber into the $NO_x$ measurement chamber and having an adjusted oxygen concentration, the $NO_x$ sensor control apparatus including a first pumping current detector for detecting a first pumping current flowing between the paired first electrodes of the first pumping cell; and a second pumping current detector for detecting the second pumping current flowing between the paired second electrodes of the second pumping cell; and the vehicle control apparatus comprising:

a receiving unit for receiving from the $NO_x$ sensor control apparatus the first pumping current, the second pumping current, first pressure correction information set for the $NO_x$ sensor, and second pressure correction information set for the $NO_x$ sensor;

an oxygen concentration calculation unit programmed to calculate an oxygen concentration of the to-be-measured gas based on the first pumping current and programmed to correct the calculated oxygen concentration in accordance with the following equation:

$$O_{P_o} = O_P\left(\frac{k_2 + P}{P}\right)\left(\frac{P_o}{k_2 + P_0}\right)$$

where $O_p$ represents an oxygen concentration value calculated from the first pumping current before pressure correction at pressure P; $O_{po}$ represents oxygen concentration after pressure correction at pressure Po; P represents the pressure (kPa) of the to-be-measured gas; Po represents atmospheric pressure; and $k_2$ represents a predetermined oxygen pressure correction coefficient; and an $NO_x$ concentration calculation unit programmed to calculate an $NO_x$ concentration of the to-be-measured gas based on the second pumping current and programmed to correct the calculated $NO_x$ concentration in accordance with the following equation:

$$NO_{x_{P_o}} = NO_{x_P}\left(\frac{k_1 + P}{P}\right)\left(\frac{P_o}{k_1 + P_0}\right)$$

where $NO_{xp}$ represents a $NO_x$ concentration value calculated from the second pumping current before pressure correction at pressure P; $NO_{xpo}$ represents $NO_x$ concentration after pressure correction at pressure Po; P represents the pressure (kPa) of the to-be-measured gas; Po represents atmospheric pressure; and $k_1$ represents a predetermined $NO_x$ pressure correction coefficient, wherein the $NO_x$ concentration calculation unit is programmed to calculate the $NO_x$ concentration of the to be measured gas based on the second pumping current and corrected in accordance with the pressure of the to-be-measured gas, the predetermined $NO_x$ pressure correction coefficient, and the corrected oxygen concentration calculated by the oxygen concentration calculation unit.

* * * * *